(12) United States Patent
Penny et al.

(10) Patent No.: US 10,434,297 B2
(45) Date of Patent: Oct. 8, 2019

(54) CONNECTOR

(71) Applicant: YUKON MEDICAL, LLC, Morrisville, NC (US)

(72) Inventors: Matthew R. Penny, Cary, NC (US); Theodore J. Mosler, Raleigh, NC (US)

(73) Assignee: YUKON MEDICAL, LLC, Morrisville, NC (US)

( * ) Notice: Subject to any disclaimer, the term of this patent is extended or adjusted under 35 U.S.C. 154(b) by 916 days.

(21) Appl. No.: 14/378,570

(22) PCT Filed: Feb. 13, 2013

(86) PCT No.: PCT/US2013/025910
§ 371 (c)(1),
(2) Date: Aug. 13, 2014

(87) PCT Pub. No.: WO2013/123028
PCT Pub. Date: Aug. 22, 2013

(65) Prior Publication Data
US 2015/0001845 A1 Jan. 1, 2015

Related U.S. Application Data

(60) Provisional application No. 61/598,091, filed on Feb. 13, 2012.

(51) Int. Cl.
A61M 39/10 (2006.01)

(52) U.S. Cl.
CPC ..... *A61M 39/10* (2013.01); *A61M 2039/1033* (2013.01); *A61M 2039/1088* (2013.01)

(58) Field of Classification Search
CPC ............. A61M 2039/1033; A61M 2039/1088
(Continued)

(56) References Cited

U.S. PATENT DOCUMENTS

| 4,810,241 | A | | 3/1989 | Rogers | |
|---|---|---|---|---|---|
| 5,122,123 | A | * | 6/1992 | Vaillancourt | ......... A61M 39/14 604/192 |

(Continued)

FOREIGN PATENT DOCUMENTS

| DE | 9320713 U1 | 3/1995 |
|---|---|---|
| DE | 29818311 U1 | 1/1999 |

(Continued)

OTHER PUBLICATIONS

European Patent Office; Extended European Search Report for Application No. 13749661.8 dated Jun. 19, 2015, 6 Pages.

(Continued)

*Primary Examiner* — Anna M Momper
*Assistant Examiner* — Fannie C Kee
(74) *Attorney, Agent, or Firm* — Christopher J. Knors; Moore & Van Allen PLLC

(57) ABSTRACT

A connector having a housing with a longitudinal axis normal to a base, and a wall projecting from the base, the wall having a plurality of cut-outs formed through the wall, the plurality of cut-outs extending in a partial helix configuration about the longitudinal axis of the housing. A first solid section extends from the base parallel to the longitudinal axis of the housing, and a second solid section extends from the base parallel with the first solid section, the first and second solid sections separating at least one of the plurality of cut-outs.

9 Claims, 3 Drawing Sheets

(58) Field of Classification Search
USPC .................. 285/332, 332.1; 604/533–535
See application file for complete search history.

(56) References Cited

U.S. PATENT DOCUMENTS

| | | | |
|---|---|---|---|
| 5,125,915 A * | 6/1992 | Berry | A61M 39/0613 |
| | | | 285/309 |
| 5,188,620 A | 2/1993 | Jepson | |
| 5,242,425 A * | 9/1993 | White | A61M 39/165 |
| | | | 604/256 |
| 5,344,414 A | 9/1994 | Lopez et al. | |
| 5,417,672 A * | 5/1995 | Nita | A61B 17/22012 |
| | | | 601/2 |
| 5,472,434 A | 12/1995 | Lechleiter | |
| 5,591,138 A * | 1/1997 | Vaillancourt | A61M 5/3271 |
| | | | 604/192 |
| 5,738,143 A * | 4/1998 | Faughn | F16L 37/373 |
| | | | 137/614.03 |
| 5,741,084 A * | 4/1998 | Del Rio | A61B 17/1633 |
| | | | 285/361 |
| 5,746,727 A * | 5/1998 | Graves | A61M 25/0631 |
| | | | 604/198 |
| 6,612,624 B1 | 9/2003 | Segal | |
| 7,678,101 B2 * | 3/2010 | Sage | A61M 39/1011 |
| | | | 604/533 |
| 2002/0173748 A1 * | 11/2002 | McConnell | A61J 1/2096 |
| | | | 604/167.02 |
| 2003/0036735 A1 | 2/2003 | Jepson | |
| 2003/0208165 A1 | 11/2003 | Christensen | |
| 2006/0271015 A1 | 11/2006 | Mantell | |
| 2007/0007478 A1 | 1/2007 | Leinsing | |
| 2007/0088327 A1 | 4/2007 | Guala | |
| 2007/0156118 A1 * | 7/2007 | Ramsey | A61M 39/20 |
| | | | 604/533 |
| 2008/0108956 A1 | 5/2008 | Lynn | |
| 2009/0105692 A1 | 4/2009 | Lopez | |
| 2010/0049144 A1 * | 2/2010 | McConnell | A61J 1/2096 |
| | | | 604/244 |
| 2010/0147297 A1 * | 6/2010 | Brewer | A61M 16/0816 |
| | | | 128/202.27 |
| 2011/0266477 A1 | 11/2011 | Stroup | |

FOREIGN PATENT DOCUMENTS

| | | |
|---|---|---|
| EP | 2153864 A1 | 2/2010 |
| WO | WO 2011/156521 | 12/2011 |

OTHER PUBLICATIONS

The International Bureau of WIPO, International Application No. PCT/US2013/025910, International Preliminary Report on Patentability dated Aug. 28, 2014, 8 pages.

Korean Intllectual Property Office, International Application No. PCT/US2013/025910 International Search Report and Written Opinion dated Jun. 2, 2013, pp. 1-12.

European Patent Office; Office Action for European Patent Application No. 13749661.8 dated May 15, 2018, 7 Pages.

European Patent Office; Office Action for European Application No. 13749661.8 dated Feb. 12, 2019, 4 Pages.

* cited by examiner

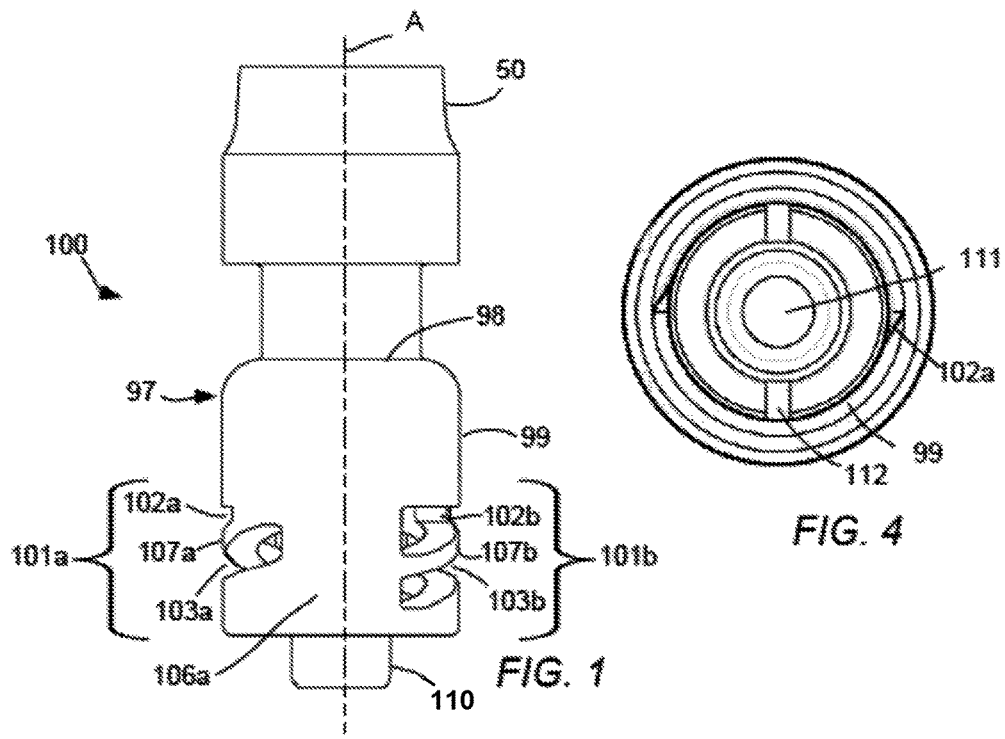
FIG. 1
FIG. 4
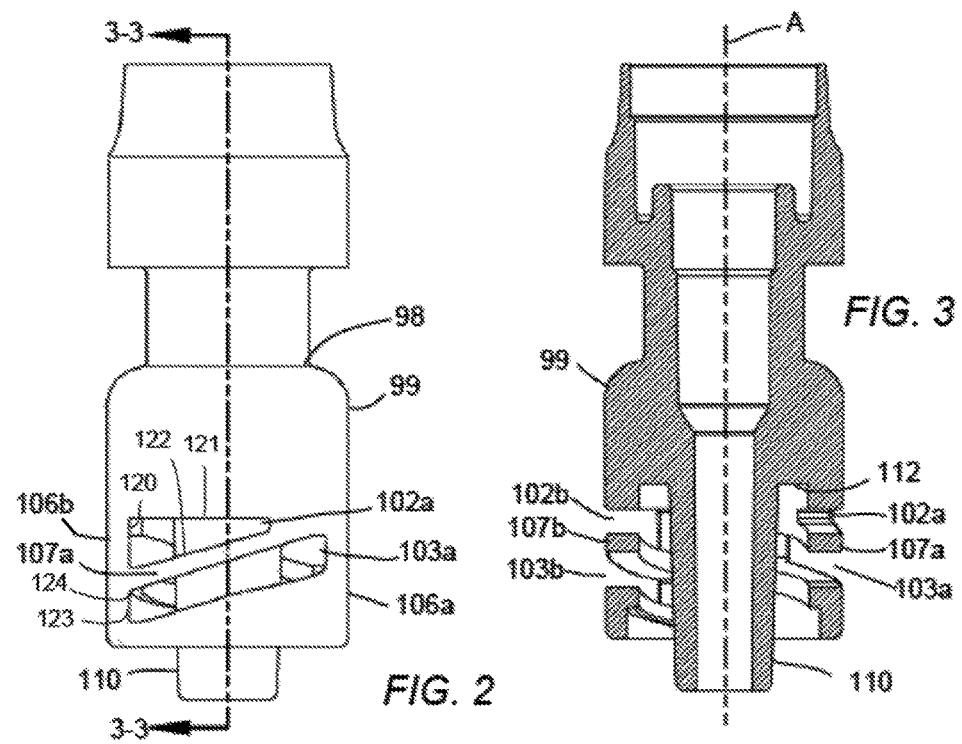
FIG. 2
FIG. 3

CONNECTOR

CROSS-REFERENCE TO RELATED APPLICATIONS

This application is filed under the provisions of 35 U.S.C. § 371 and claims the benefit of International Patent Application No. PCT/US2013/025910, filed on Feb. 13, 2013, which claims the benefit of U.S. Provisional patent application 61/598,091, filed in the United States Patent and Trademark Office on Feb. 13, 2012; all of which are hereby incorporated by reference in their entirety.

TECHNICAL FIELD

Devices for providing connection are provided. Specifically, devices comprising a housing with a base and a wall projecting from the base, the wall comprising a plurality of cut-outs formed through the wall capable of providing threading for connecting.

BACKGROUND

An internal thread is basically an undercut that does not allow free ejection from the mold. Integrally molded, internal threads are often used for medical connectors. Plastic injection molding of internal threads for certain medical devices presents challenges to designing. In general, injection molding of internal threads, such as a medicine vial cap, can be relatively easy using a slight draft on the core surface to allow the part to be stripped from the core by means of a stripper ring. Provided the draft is suitable and the plastic of proper tensile strength, the part slides off the core easily, the draft reducing the drag quickly and the soft part stripping without deformation. On the other hand, molded-in internal threads on more complex injection molded parts add to the complexity of mold and put constraints on the design. Low production prototype molds can be unscrewed by hand, but most medical device molding is required to be performed automatically. Typically, continuous molding internal threads on plastic medical devices are performed either by stripping, collapsible cores, or unscrewing devices.

Stripped internal threads involves de-mold parts with internal threads by stripping them from the core. This technique is very limited and depends on the plastic used and the thread features. Typically, only thermoplastics with a low modulus of elasticity and a high yield strain are suitable for stripping. Thus, this method is limited at least to certain plastics because during the stripping process, the elastic limit may be exceeded, resulting in defects. Rounded threads are best suited for the stripping method, which further limits design options.

A collapsible threaded core is generally used to mold internal thread forms and freely eject small to medium size parts. Collapsible cores typically result in parting lines appearing on the part due to the segments of the split core. Drawbacks of collapsible cores include flash, plastic build up on the core components requiring cleaning, inconsistent spring pressures, and/or finishing processes for core surfaces. In addition, collapsible cores are more expensive tooling options that are especially prone to wear. These drawbacks make collapsible cores less desirable.

High-quality, large production series internally threaded parts are predominately produced using un-screwing devices ("rotating cores") integrated with the mold. The majority of all thread forms (especially medium to large) are unscrewed before ejection from the mold. The basic operation is to rotate the core and retract it at the same time and at the same rate as the core is unscrewing from the part. This requires several components working in unison. Usually a rack is used to rotate a gear and an adjustable lead nut times the retraction, which requires an air cylinder or some other means of drive. Rotating cores require bearings to allow rotation of the core during the retraction. The mold typically must have a feature to keep the part from turning while the core is rotating and retracting, e.g., anti rotation lugs, which are cut into the ejection sleeve or into the stripper ring. Thus, a more complex, expensive mold is required.

SUMMARY

In a first embodiment, a connector is provided. The connector comprises a housing having a longitudinal axis normal to a base, and wall projecting from the base. The wall comprises a plurality of cut-outs formed through the wall, the plurality of cut-outs extending in a partial helix configuration about the longitudinal axis of the housing. A first solid section extends from the base parallel to the longitudinal axis of the housing, and a second solid section extends from the base parallel with the first solid section, the first and the second solid sections separating at least one of the plurality of cut-outs.

In a second embodiment, a medical device connector is provided. The medical device connector comprising a housing having a base, a male luer projecting from the base, the male luer having a longitudinal axis normal to the base, an annular wall projecting from the base and at least partially surrounding the male luer, and a plurality of cut-outs through the annular wall, the plurality of cut-outs extending in a helix configuration about the longitudinal axis of the male luer.

BRIEF DESCRIPTION OF THE DRAWINGS

FIG. 1 is a perspective view of an embodiment of the present disclosure.

FIG. 2 is perspective view of the embodiment of FIG. 1, rotated about ninety degrees and showing sectional line 3-3.

FIG. 3 is a sectional view along line 3-3 of the embodiment of FIG. 2.

FIG. 4 is a bottom view of the embodiment of FIG. 1.

DETAILED DESCRIPTION

Figure 5:
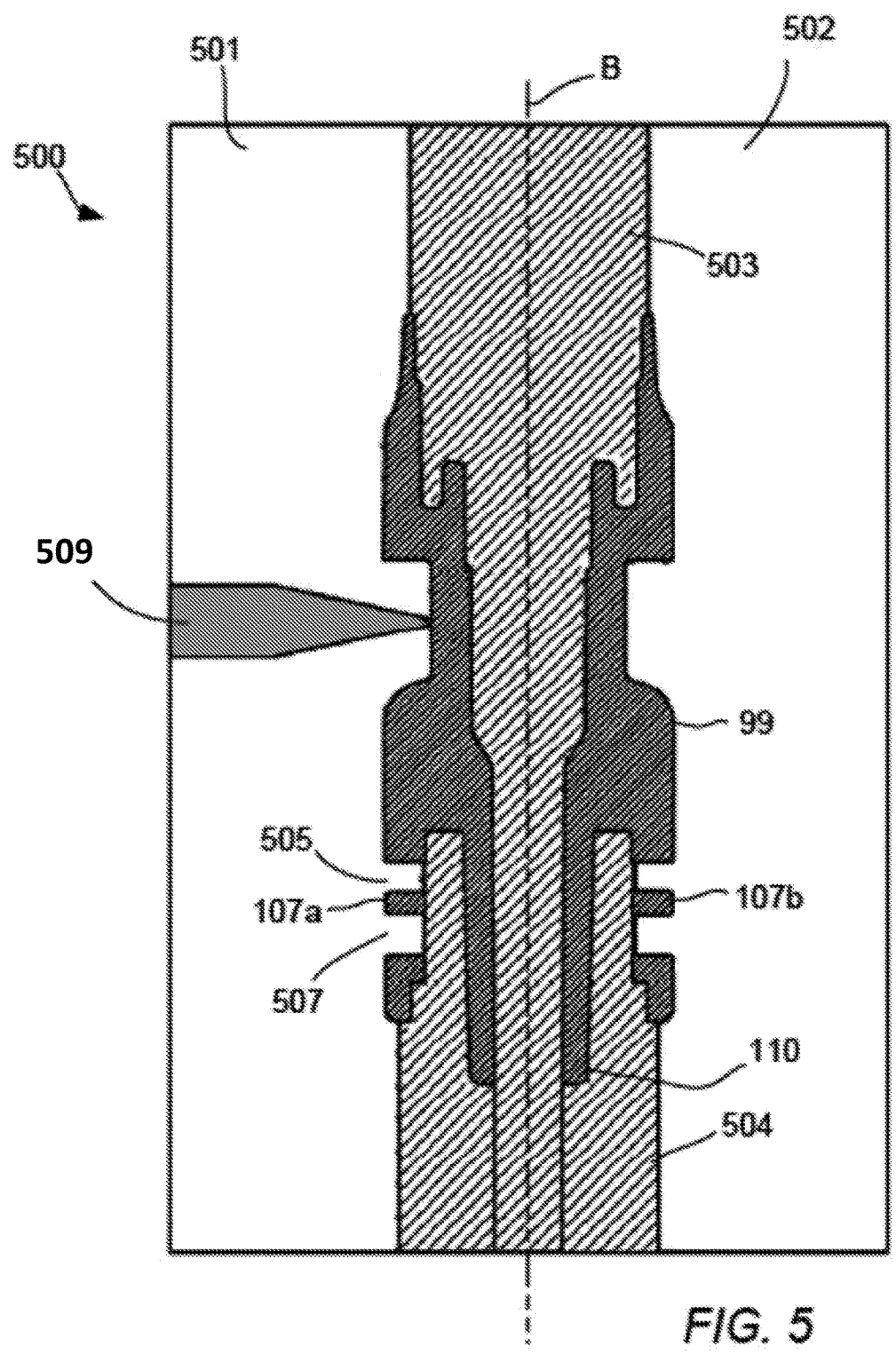
FIG. 5 is a sectional view of a molded part positioned in an exemplary mold.

A connector is disclosed comprising internal threads configured for attachment with other devices. The device is configured with a base, a wall projecting from the base, and cut-outs in the wall comprising thread-like features. The design of the present device provides for thread-like features to be formed from the exterior of the part, thus eliminating the need for unscrewing (rotating cores), and/or collapsible cores during an injection molding process.

In one aspect, the device comprises a male luer component. The male luer can be designed per the ISO 594 standards. The male luer can be at least partially surrounded by the projecting wall, which together with the thread-like features, allows for attachment with other devices, such as devices commonly used in the medical field. The manufacturing of the thread-like features avoids complex and expensive mold tooling. In one aspect, the thread-like features can be formed by the utilization of stationary mold members incorporated in the mold tool. Such mold members provide for shutoff on the portion of the tool forming the thread-like features and male luer.

The following description and examples illustrate some exemplary embodiments of the disclosed disclosure in detail. Those of skill in the art will recognize that there may be numerous variations and modifications of this disclosure that may be encompassed by its scope. Accordingly, the description of a certain exemplary embodiment is not intended to limit the scope of the present disclosure.

The terminology used herein is for the purpose of describing particular embodiments only and is not intended to be limiting of the inventive subject matter. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

When an element is referred to herein as being "connected" or "coupled" to another element, it can be directly connected or coupled to the other element or intervening elements may be present. In contrast, when an element is referred to herein as being "directly connected" or "directly coupled" to another element, there are no intervening elements present. In addition, a statement that a first element is "on" a second element is synonymous with a statement that the second element is "on" the first element.

Although the terms "first", "second", etc. may be used herein to describe various elements, components, regions, sections and/or parameters, these elements, components, regions, sections and/or parameters should not be limited by these terms. These terms are only used to distinguish one element, component, region, or section from another region, or section. Thus, a first element, component, region, or section discussed below could be termed a second element, component, region, or section without departing from the teachings of the present disclosure. Relative terms, such as "lower", "bottom", "below", "upper", "top" or "above," may be used herein to describe one element's relationship to another element as illustrated in the Figures. Such relative terms are intended to encompass different orientations of the device in addition to the orientation depicted in the Figures. For example, if the device in the Figures is turned over, elements described as being on the "lower" side of other elements would then be oriented on "upper" sides of the other elements. The exemplary term "lower", can therefore, encompass both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

The term "annular" as used herein includes the dictionary definition of related to or forming a ring, and is inclusive of a partial or complete ring-shaped structure, for example, a tubular structure, a "c-shape," a "u-shape," or an "o-shape."

Throughout the specification, the term "fluid" as used herein is inclusive of gaseous, liquid, and combinations of gas and liquid medium unless specifically designated as limited to a particular medium.

Throughout the specification, the term "media" as used herein is inclusive of fluids and solid form mediums unless specifically designated as limited to a particular medium.

Throughout the specification, the term "liquid" as used herein is inclusive of suspensions, oil-in-water emulsions, water-in-oil emulsions, and liquids with or without dissolved, dispersed, or contained solids irrespective of the size of the solids or the amount present.

Embodiments of the present disclosure will now be described more fully hereinafter with reference to the accompanying drawings, in which exemplary embodiments are shown. This present disclosure may, however, be embodied in many different forms and should not be construed as limited to the embodiments set forth in the drawings. Rather, these embodiments are provided so that this disclosure will be thorough and complete, and will fully convey the scope of the disclosure to those skilled in the art. Like numbers refer to like elements throughout.

With reference to FIG. 1 a perspective view of connector 100 is shown. Connector 100 comprises a housing 97 having longitudinal axis A base 98, and wall 99 projecting from base 98; the wall comprising first solid section 106a (second solid section 106b being on the opposite side of wall 99), a plurality of cut-outs, shown as first pair of cut-outs 101a having cut-out 102a shown positioned above cut-out 103a, respectively, and second pair of cut-outs 101b having cut-out 102b positioned above cut-out 103b, respectively. Pairs of cutouts 101a and 101b are shown separated from each other by solid section 107. Cut-outs 102a, 103a are also separated by third solid section 107a of wall 99, third solid section 107a extending from first solid section 106a to second solid section 106b, likewise, cut-outs 102b, 103b are separated by fourth solid section 107b that also extends from first solid section 106a to second solid section 106b. Cut-outs 102a, 102b, 103a, 103b, and third/fourth solid sections 107a, 107b, are shown extending in a helix configuration about the longitudinal axis A. Exemplary adapter 50 projects from housing 97 and be any type of internally/externally threaded, non-threaded, luer adapter, etc., for coupling with connector 100. Cut-out pairs 101a, 101b are configured to receive luer threading.

In one aspect, cut-out pairs 101a, 101b are configured as internal threading elements for engaging another device comprising suitably configured lugs. The engagement of the internal threading elements of connector 100 and lugs can be of a locking/reversible relationship, for example, as used in coupling fluid connectors used in the medical field. In one aspect, cut-out pairs 101a, 101b are configured to receive female conical lock fittings with lugs meeting ISO 594 specifications, for example, Variant A, Variant B, or Variant C of ISO 594-2:1998.

In one aspect, connector 100 is a medical connector configured for engagement with a female luer-type connector, female valves connector, etc. Thus, in this aspect with reference to FIGS. 1 and 2, male luer 110 with longitudinal axis aligned with that of axis A, projects from base 98 of housing 97 and is at least partially surrounded by wall 99. In one aspect, wall 99 is annular or tubular in shape and completely surrounds male luer 110. As shown in FIG. 2, cutout 102a is positioned above cut-out 103a, separated by third solid section 107a extending in a helix configuration from first solid section 106a to second solid section 106b.

As shown, wall 99 is integral with housing 97 and base 98. In one aspect, wall 99 (and base 98) is configured to at least partially rotate about housing 97 and/or male luer 110. In this aspect, wall 99 is a rotatable collar about male luer 110 and can be engaged with a corresponding device without having to torque housing 97 of connector 100.

Still referring to FIGS. 2-3, cut-out 102a is polygonal shaped, defined by at least first edge 120 that is substantially parallel to axis A (and section line 3-3), and second edge 121 that is substantially perpendicular to axis A. Third edge 122 corresponds to that of third solid section 107a. Cut-out 103a is generally rectangular in shape and has fourth edge 123 substantially parallel to axis A, and fifth edge 124 corresponding to that of third solid section 107a. In one aspect, first pair of cut-outs 101a is identical to that of second pair of cut-outs 101b.

FIG. 4 depicts a bottom view of connector 100, showing conduit 111 of male luer 110 and base 98, with molded surfaces 112 positioned about luer 110. Portions of cut-outs from pairs 101a, 101b can be seen.

Figure 6:
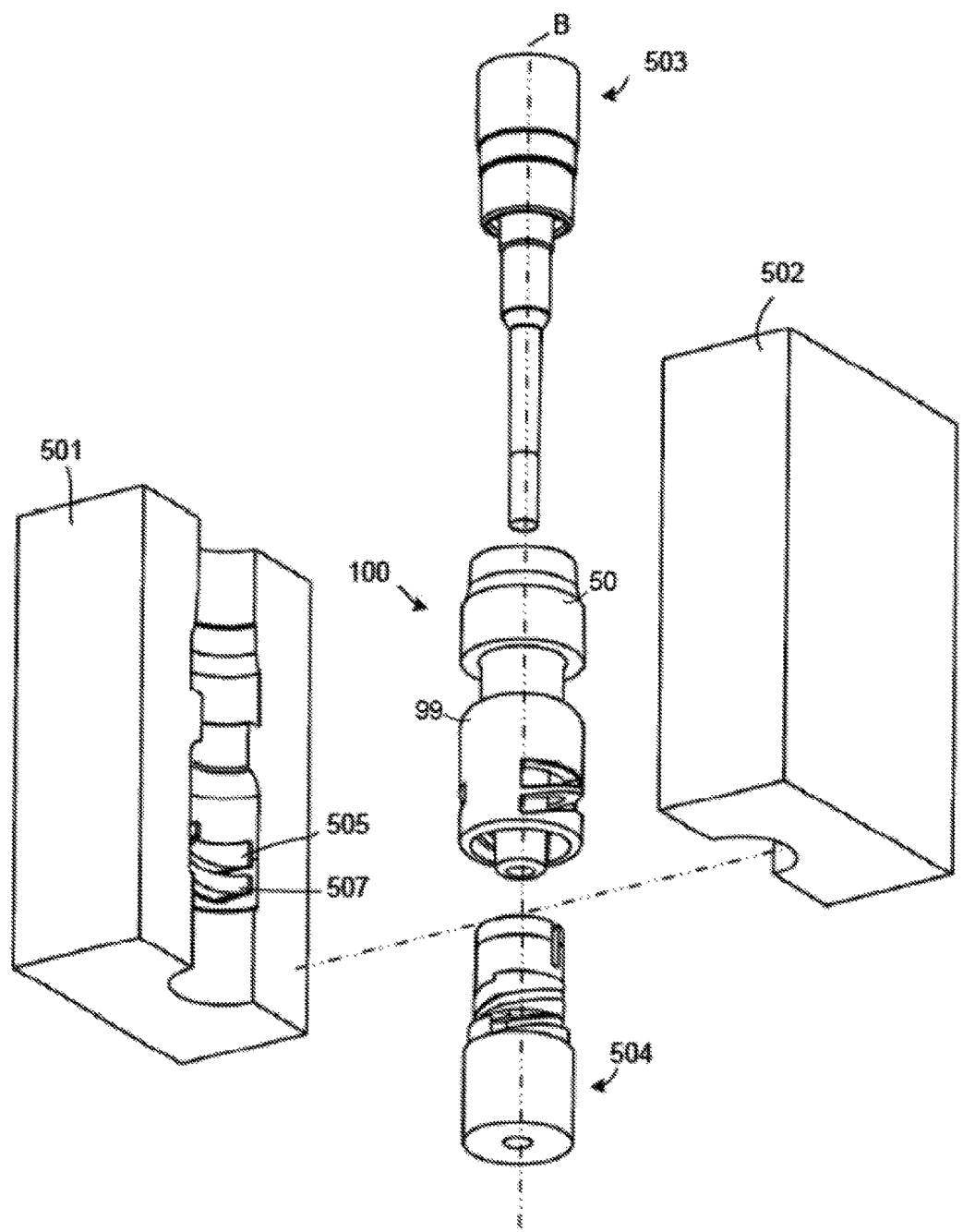
FIG. 6 is an exploded view of an exemplary mold for the embodiment of FIG. 1.

FIGS. 5-6 depict exemplary mold 500, with first half 501 and second half 502 separable about first core pin 503 and second core pin 504 for forming male luer and adapter 50. Mold members 505, 507 projecting from interior surface of mold halves 501, 502 provide for pairs of cut-puts parting along line B. Mold 500 is shown with side gate 509. Other gating, core pin assemblies, adapter configurations, and other designs can be used.

All of the components of the proposed embodiments may be injection molded or combined with injection molding processes. Alternate manufacturing methods can include compression or transfer molding. Design intent can be such that components are molded with simple open/close tooling to reduce tooling cost and cycle times. The cut-outs can, alternatively, be formed by laser cutting.

Where feature definition may not be able to be achieved by single tool molding; ultrasonic welding, adhesives or mechanical retention may be employed to join one or more components. Furthermore, where dissimilar materials may be advantageous, a 2-shot molding technique may be utilized, such as creating a non-slip and or soft surface to the housing in combination with rigid or harder durometer male luer.

The disclosed and described device provides multiple advantageous features, including, but not limited to reduced complexity and/or cost of tooling, increased cycle, and design options, when compared to contemporary devices of this kind.

The above description discloses several configurations, embodiments, and methods. These descriptions are susceptible to modifications in the methods and configurations, as well as alterations in the fabrication methods and equipment. Such modifications will become apparent to those skilled in the art from a consideration of this disclosure or practice of the disclosure. Consequently, it is not intended that this disclosure be limited to the specific embodiments disclosed herein, but that it cover all modifications and alternatives coming within the true scope and spirit of the claims.

Furthermore, while certain embodiments of the present disclosure have been illustrated with reference to specific combinations of elements, various other combinations may also be provided without departing from the teachings of the present disclosure. Thus, the present disclosure should not be construed as being limited to the particular exemplary embodiments described herein and illustrated in the Figures, but may also encompass combinations of elements of the various illustrated embodiments and aspects thereof.

The invention claimed is:

1. A connector comprising:
   a housing having a longitudinal axis normal to a base;
   a wall projecting from the base, the wall comprising a first solid section and a second solid section;
   a first pair of cut-outs formed through the wall, the first pair of cut-outs defined by a third solid section;
   a second pair of cut-outs formed through the wall, the second pair of cut-outs defined by a fourth solid section, and
   a male luer having a longitudinal axis, the male luer extending from the base parallel with the wall, the male luer at least partially surrounded by the wall,
   wherein the first pair of cutouts, the second pair of cutouts, the third solid section, and the fourth solid section are in a complementary partial helix configuration around the longitudinal axis of the housing and around the longitudinal axis of the male luer,
   wherein the first pair of cut-outs and the second pair of cut-outs are configured to receive locking lugs, and
   wherein the first and second solid sections separate the first pair of cut-outs from the second pair of cutouts.

2. The connector of claim 1, wherein the first pair of cutouts and the second pair of cut-outs are configured to receive locking lugs in accordance with ISO 594-2:1998 specifications.

3. The connector of claim 1, wherein the third solid section provides at least one edge for the first pair of cut-outs, and the fourth solid section provides at least one edge for the second pair of cut-outs.

4. The connector of claim 1, wherein the wall is configured to at least partially rotate about the longitudinal axis of the housing and base.

5. A medical device connector comprising:
   a housing having a base and a longitudinal axis;
   a male luer projecting from the base, the male luer having a longitudinal axis normal to the base;
   an annular wall extending from the base parallel with the longitudinal axis of the male luer, the annular wall at least partially surrounding the male luer, the wall comprising a first solid section and a second solid section; and
   a first pair of cut-outs formed through the wall, the first pair of cut-outs defined by a third solid section; and
   a second pair of cut-outs formed through the wall, the second pair of cut-outs defined by a fourth solid section,
   wherein the first pair of cut-outs, the second pair of cut-outs, the third solid section, and the fourth solid section of the wall are in a complementary partial helix configuration around the longitudinal axis of the housing and around the longitudinal axis of the male luer,
   wherein the first pair of cut-outs and the second pair of cut-outs are configured to receive locking lugs, and
   wherein the first and second solid sections separate the first pair of cut-outs from the second pair of cutouts.

6. The medical device connector of claim 5, wherein the first pair of cut-outs, the second pair of cut-outs, the third solid section, and the fourth solid section of the wall completely surround the male luer.

7. The medical device connector of claim 5, wherein the first pair of cut-outs and the second pair of cut-outs are configured to receive locking lugs in accordance with ISO 594-2: 1998 specifications.

8. The connector of claim 5, wherein the third solid section provides at least one edge for the first pair of cut-outs, and the fourth solid section provides at least one edge for the second pair of cut-outs.

9. The connector of claim 5, wherein the annular wall is configured to at least partially rotate about the longitudinal axis of the male luer and base.

\* \* \* \* \*

UNITED STATES PATENT AND TRADEMARK OFFICE
CERTIFICATE OF CORRECTION

PATENT NO. : 10,434,297 B2
APPLICATION NO. : 14/378570
DATED : October 8, 2019
INVENTOR(S) : Matthew R. Penny and Theodore J. Mosler It is certified that error appears in the above-identified patent and that said Letters Patent is hereby corrected as shown below:

On the Title Page

IN THE ABSTRACT (57):
Please change Line 9 to:
the second solid sections separating at least one of the plurality In the Claims In Column 6, Claim 1, please change Line 18 to:
wherein the first and the second solid sections separate the In Column 6, Claim 5, please change Line 53 to:
wherein the first and the second solid sections separate the Signed and Sealed this
Thirty-first Day of December, 2019

Andrei Iancu
*Director of the United States Patent and Trademark Office*